(12) United States Patent
Tsaur et al.

(10) Patent No.: US 10,441,823 B2
(45) Date of Patent: Oct. 15, 2019

(54) OXYGEN-PROVIDING MATERIAL WITH THE FUNCTION OF SKIN WHITENING

(71) Applicants: Garry Tsaur, Rowland Heights, CA (US); Frank Tsaur, Rowland Heights, CA (US); Ting-Hua Wang, Rowland Heights, CA (US)

(72) Inventors: Garry Tsaur, Rowland Heights, CA (US); Frank Tsaur, Rowland Heights, CA (US); Ting-Hua Wang, Rowland Heights, CA (US)

(*) Notice: Subject to any disclaimer, the term of this patent is extended or adjusted under 35 U.S.C. 154(b) by 80 days.

(21) Appl. No.: 15/584,621

(22) Filed: May 2, 2017

(65) Prior Publication Data
US 2018/0111012 A1    Apr. 26, 2018

(30) Foreign Application Priority Data
Oct. 25, 2016   (CN) .......................... 2016 1 0935074

(51) Int. Cl.
| | | |
|---|---|---|
| *A61Q 19/02* | (2006.01) | |
| *A61K 8/02* | (2006.01) | |
| *A61K 8/04* | (2006.01) | |
| *A61K 8/22* | (2006.01) | |
| *A61Q 19/08* | (2006.01) | |
| *A61Q 19/00* | (2006.01) | |

(52) U.S. Cl.
CPC ................ *A61Q 19/02* (2013.01); *A61K 8/02* (2013.01); *A61K 8/046* (2013.01); *A61K 8/22* (2013.01); *A61Q 19/08* (2013.01); *A61K 2800/22* (2013.01); *A61K 2800/222* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 2002/0176903 A1* | 11/2002 | Kuno | ................... | A61K 8/0212 424/777 |
| 2006/0094634 A1* | 5/2006 | Jekel | ................... | C11D 3/3707 510/446 |
| 2013/0061883 A1* | 3/2013 | Miravet Celades | ..... | A61K 8/38 134/26 |

OTHER PUBLICATIONS

Machine translation, CN 10680032 A (2017).*

* cited by examiner

*Primary Examiner* — Bethany P Barham
*Assistant Examiner* — Barbara S Frazier
(74) *Attorney, Agent, or Firm* — WPAT, PC (57) ABSTRACT

The present invention provides an oxygen-providing material with the function of skin whitening, characterized in that said oxygen-providing material comprises a solid oxygen source, an activator, and a catalyst; wherein the solid oxygen source is selected from the group consisting of peroxide and percarbonate; wherein the oxygen-providing material with the function of skin whitening can be placed in household products, said household products comprising respirator, mask, facial mask, bra, chest paste, spill proof pad, sanitary napkin, diaper, panty liner, disposable hygiene product, band-aids, wrapping sponge, and box-shaped container.

6 Claims, 4 Drawing Sheets

OXYGEN-PROVIDING MATERIAL WITH THE FUNCTION OF SKIN WHITENING

BACKGROUND OF THE INVENTION

1. Field of the Invention

The present invention relates to a gaseous skin oxygen-providing and whitening product and its usage, which belongs to the technical field of medical cosmetology.

2. Description of the Prior Art

The existence of human skin melanin mainly serves to fight against the harm ultraviolet rays cause the skin. However, according to the aesthetic value of modern people, melanin poses huge problems for many people, such as freckle, senile plaque, chloasma, Tinea Versicolor, Areola pigment sedimentation and blackening, private area melanin sedimentation.

There are many different factors leading to melanin sedimentation, such as genetic factors, skin aging, lack of oxygen in skin, excessive friction, sequela of hormone-containing external drugs, pregnancy, secretion of estrogen, and so on.

The production of melanin by melanophore mainly takes place at the stratum basale of skin epidermis, which through metabolism, is gradually pushed to the stratum spinosum, the stratum granulosum, the stratum lucidum, and at last transported to the outermost layer of the epidermis, i.e. the stratum corneum.

Commercially available whitening products are mostly liquid, paste, or emulsion, which are very difficult to be delivered to the stratumbasale due to large molecular weight. This is the main reason why the whitening effects are not ideal. Currently, methods of removing melanin include surgery, using laser to remove melaninbut there is some risk for this method. If laser is applied to the dermis, it's easy to cause permanent damages to the skin.

To solve the technical defects of the prior art, the present invention provides a gaseous skin oxygen-providing and whitening product with good whitening effects and safety, which is an important issue that the present invention aims to solve.

SUMMARY OF THE INVENTION

The present invention provides a gaseous skin oxygen-providing and whitening material with good whitening effects and safe. This material can react with water in body fluids such as sweat secreted by human body to produce whitening gas, containing oxygen and reactive oxygen species (ROS). Besides the oxygen needed for healthy skin respiration, the present invention provides gaseous ROS with the function of skin whitening, including hydroperoxyl (HOO$^-$), superoxide anion, and hydroperoxyl radical (HOO$^-$). Because the molecular weight of ROS is very low, with the diameter of around 1 nm, ROS can pass through the skin gap of the epidermis (the diameter of the skin gap of the epidermis ranges from 200 nm to 80000 nm), to reach the skin stratum basale layer and react with melanin, rendering the melanin to be shallowed, or even transparent. The whitening material is in a solid state, which reacts with water in body fluids such as sweat which is more gentle than in liquid state, and long term providing whitening gas.

To solve the above-mentioned technical problem, the present invention aims to provide a material providing skin-whitening gas, wherein said material comprises a solid oxygen source, a solid activator, and a solid catalyst; wherein the solid oxygen source is selected from the group consisting of peroxide and percarbonate; wherein the solid activator is anilide compound; wherein the solid catalyst is catalase; wherein the material can react with fluid to produce whitening gas.

To achieve the above-mentioned aim of the present invention, the peroxide is selected from the group consisting of calcium peroxide, magnesium peroxide, sodium peroxide, potassium peroxide, sodium percarbonate, and calcium percarbonate.

To achieve the above-mentioned aim of the present invention, the anilide compound is selected from the group consisting of tetraacetyl ethylene diamine (TAED), sodium nonanoyloxy benzene sulfonate (NOBS), tetraacetyl glycoluril, pentaacetyl glucose, N-acetyl phthalimid, 1-acetyl ethyl benzoate, triacetyl ethanolamine, and nonanoyl acetyl phenyl tosylate.

To achieve the above-mentioned aim of the present invention, the mass ratio between the activator and the solid oxygen source ranges from 0.5:100 to 10:100; the mass ratio between the catalyst and the solid oxygen source ranges from 0.5:100 to 5:100.

To achieve the above-mentioned aim of the present invention, the mass ratio between the activator and the solid oxygen source ranges from 2:100 to 3:100; the mass ratio between the catalyst and the solid oxygen source ranges from 1.5:100 to 2.5:100.

To achieve the above-mentioned aim of the present invention, citric acid can be further added into the material with the function of skin whitening, the mass ratio between the citric acid and the solid oxygen source ranges from (5-8):(2-5).

To achieve the above-mentioned aim of the present invention, the particle size of the material with the function of skin whitening ranges from 2000 meshes to 2 mm.

To achieve the above-mentioned aim of the present invention, the material with the function of skin whitening can be placed in household hygiene products, said household hygiene products comprising respirator, mask, facial mask, bra, chest paste, spill proof pad, sanitary napkin, diaper, panty liner, disposable hygiene product, band-aids, wrapping sponge, and box-shaped container.

To achieve the above-mentioned aim of the present invention, the whitening gas contains oxygen or reactive oxygen species (ROS).

Another aim of the present invention is to provide a skin whitening structure, wherein the skin whitening structure packages the above-mentioned material with breathable materials, the particle size of the material ranges from 2000 meshes to 2 mm, the breathable material contains small pores, the diameter of small pores are less than the particle size of the material, and the diameter of small pores are larger than the whitening gas.

DETAILED DESCRIPTION OF THE PREFERRED EMBODIMENT

The present invention is illustrated by the embodiments below. However, the present invention is not limited by the embodiments below.

Figure 1:
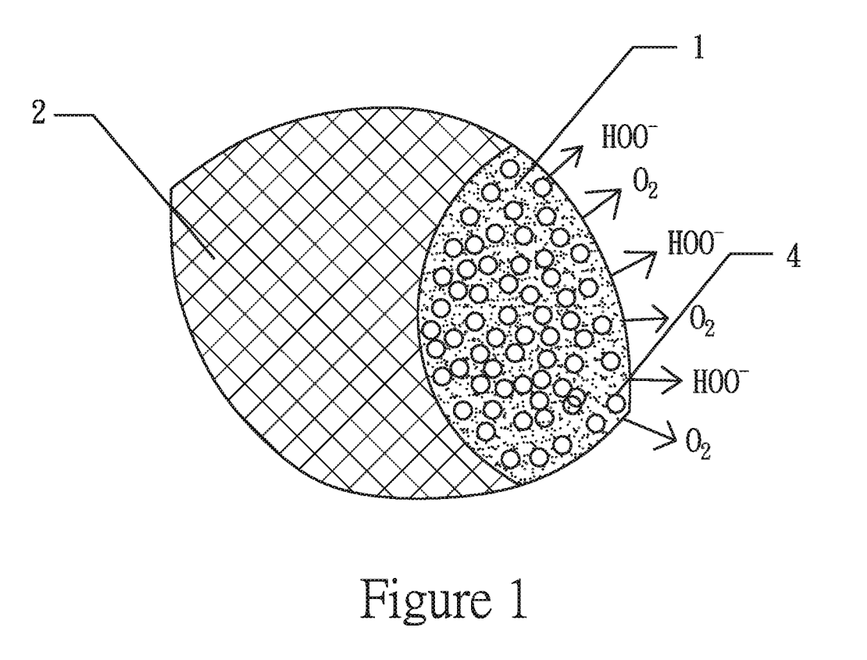
FIG. 1 represents a structural diagram of an oxygen-providing material containing gradually releasing ROS and oxygen with the function of skin whitening.
Figure 2:
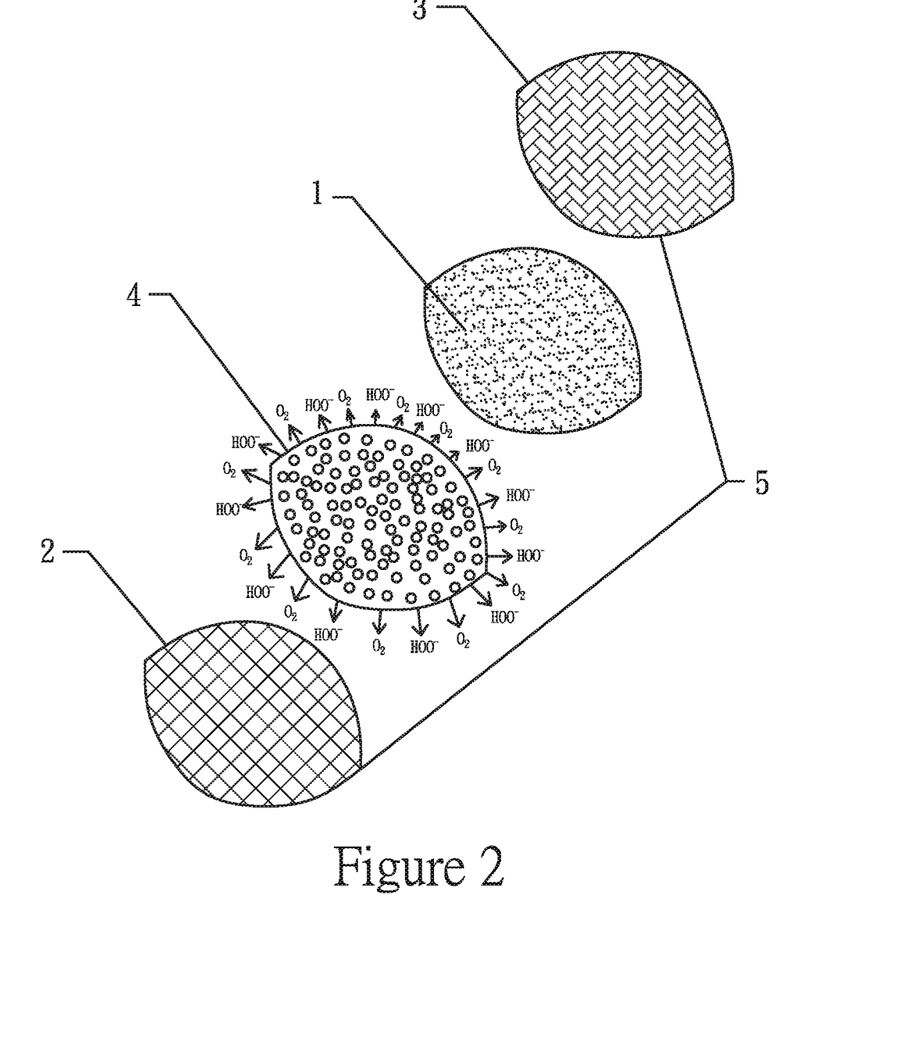
FIG. 2 represents a structural diagram of a functional unit located at the inner surface of the inner core.
Figure 3:
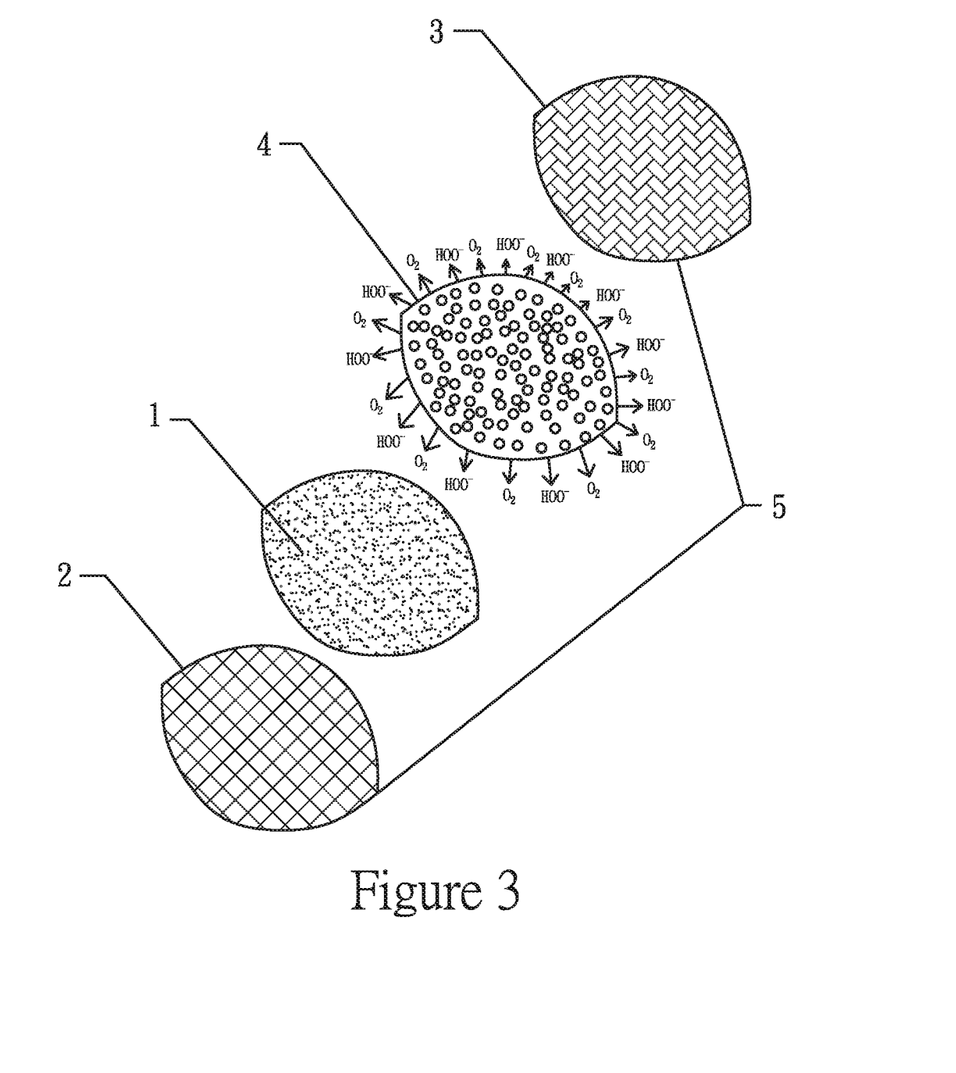
FIG. 3 represents a structural diagram of a functional unit located at the outer surface of the inner core.
Figure 4:
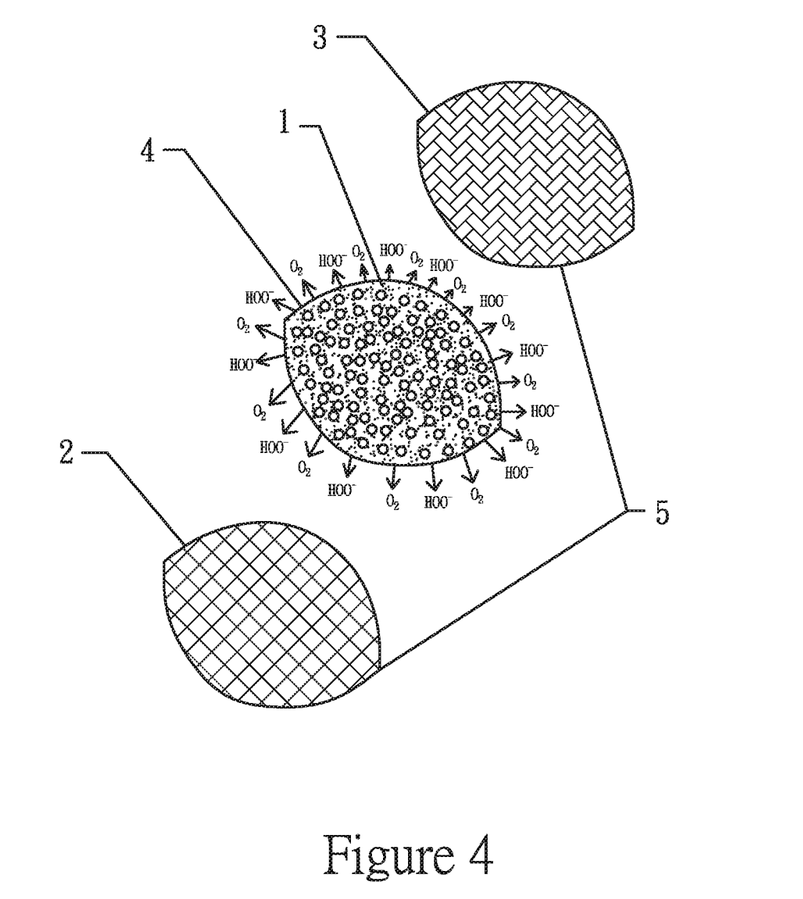
FIG. 4 represents a structural diagram of a functional unit located within inner cores.

As is illustrated by FIGS. 1, 2 and 3, an oxygen-providing material containing gradually releasing ROS and oxygen with the function of skin whitening comprises inner core 1 and outer coating layer 5. Inner core 1 is used to fix a functional unit 4 containing oxygen-providing material with the function of skin whitening. Inner core 1 is made of water-absorbing materials. Outer coating layer 5 is used to coat inner core 1. Functional unit 4 can be evenly distributed at the inner surface of inner core 1, functional unit 4 can be evenly distributed at the outer surface of inner core 1, and functional unit 4 can also be evenly distributed between inner surfaces of inner core 1. Outer coating surface 5 comprises inner layer 2 and outer layer 3, wherein inner layer 2 is a breathable structure made of skin-friendly materials, and outer layer 3 can be made of breathable or non-breathable materials. To achieve better effects of gradually releasing ROS and oxygen, outer layer 3 can be preferably made of non-breathable materials. Functional unit 4 is made of a mixture of a solid oxygen source, a catalyst, and an activator.

A Formula Composition of an Oxygen-Providing Material with the Function of Skin Whitening An oxygen-providing material with the function of skin whitening is made of whitening formula 1 made of a mixture of solid oxygen source calcium peroxide, catalyst catalase, and activator tetraacetyl ethylene diamine;

wherein the mass ratio between the catalase and the calcium peroxide is 1:200;

wherein the mass ratio between the tetraacetyl ethylene diamine and the calcium peroxide is 1:200;

wherein the particle size of the oxygen-providing material with the function of skin whitening is 60 meshes.

The solid oxygen source calcium peroxide ($CaO_2$), the catalyst catalase (CAT) and the activator tetraacetyl ethylene diamine (TAED) is mixed evenly, and water secreted by skin (sweat) or body fluid (urine or blood), or water in the air (moisture) is used to react with the oxygen-providing material with the function of skin whitening, alternatively aqueous liquid is prepared to react with the oxygen-providing material with the function of skin whitening when used.

The reaction formula is $CaO_2 + H_2O \rightarrow Ca(OH)_2 + O_2$; similar to weak acid, the intermediate of the above reaction, i.e. hydrogen peroxide ($H_2O_2$) is dissociated into hydrogen peroxide anion in basic medium.

Hydrogen peroxide anion is a nucleophile, with the function of triggering the hydrogen peroxide to form free radical.

Both have relatively high activity, which can oxidize and break down pigments, producing a bleaching effect.

The produced gaseous active oxygen can keep a relatively high gas concentration of ROS in a coated environment.

Whitening formula 2: it is produced by a mixture of solid oxygen source calcium peroxide, catalyst catalase, and activator tetraacetyl ethylene diamine, and the adding amounts of the catalyst and the activator are changed, on the basis of whitening formula 1, wherein the mass ratio between the catalase and the calcium peroxide is 1:50;

wherein the mass ratio between the tetraacetyl ethylene diamine and the calcium peroxide is 1:40.

Whitening formula 3: it is produced by a mixture of solid oxygen source calcium peroxide, catalyst catalase, and activator tetraacetyl ethylene diamine, and the content of the catalyst and the activator are changed, on the basis of whitening formula 1, wherein the mass ratio between the catalase and the calcium peroxide is 1:20;

wherein the mass ratio between the tetraacetyl ethylene diamine and the calcium peroxide is 1:10.

Whitening formula 4: it is produced by a mixture of solid oxygen source calcium peroxide, catalyst catalase, activator tetraacetyl ethylene diamine, and citric acid, and citric acid is added on the basis of whitening formula 2, wherein the mass ratio between the catalase and the calcium peroxide is 1:50;

wherein the mass ratio between the tetraacetyl ethylene diamine and the calcium peroxide is 1:40;

wherein the mass ratio between the citric acid and the calcium peroxide is 7:4.

Whitening formula 5: the types of the solid oxygen source and the activator as well as the particle size of the products are changed on the basis of whitening formula 2, wherein the solid oxygen source is magnesium peroxide; wherein the activator is sodium nonanoyloxy benzene sulfonate; and the particle size of the product is 2000 meshes.

Whitening formula 6: the types of the solid oxygen source and the activator are changed on the basis of whitening formula 2, wherein the solid oxygen source is sodium peroxide; wherein the activator is tetraacetyl glycoluril.

Whitening formula 7: the types of the solid oxygen source and the activator as well as the particle size of the products are changed on the basis of whitening formula 2, wherein the solid oxygen source is potassium peroxide; wherein the activator is pentaacetyl glucose; wherein the particle size of the products is 2 mm.

Whitening formula 8: the types of the solid oxygen source and the activator are changed on the basis of whitening formula 2, wherein the solid oxygen source is sodium percarbonate; wherein the activator is N-acetyl phthalimid.

Whitening formula 9: the types of the solid oxygen source and the activator are changed on the basis of whitening formula 2, wherein the solid oxygen source is calcium percarbonate; wherein the activator is 1-acetyl ethyl benzoate.

Whitening formula 10: the type of the activator is changed on the basis of whitening formula 2, wherein the activator is triacetyl ethanolamine.

Whitening formula 11: the type of the activator is changed on the basis of whitening formula 2, wherein the activator is nonanoyl acetyl phenyl tosylate.

Comparison group 1: it is produced by a mixture of solid oxygen source calcium peroxide, catalyst catalase, and activator tetraacetyl ethylene diamine, and the adding amounts of the catalyst and the activator are changed, on the basis of whitening formula 1, wherein the mass ratio between the catalase and the calcium peroxide is 1:250;

wherein the mass ratio between the tetraacetyl ethylene diamine and the calcium peroxide is 11:100.

Comparison group 2: it is produced by a mixture of solid oxygen source calcium peroxide, catalyst catalase, and activator tetraacetyl ethylene diamine, and the adding amounts of the catalyst and the activator are changed, on the basis of whitening formula 1, wherein the mass ratio between the catalase and the calcium peroxide is 5.5:100;

wherein the mass ratio between the tetraacetyl ethylene diamine and the calcium peroxide is 1:250.

Comparison group 3: it is produced by a mixture of solid oxygen source calcium peroxide, and catalyst catalase, and tetraacetyl ethylene diamine is removed on the basis of whitening formula 2, wherein the catalase accounts for 2% of the quality percentage of the calcium peroxide.

Comparison group 4: only solid oxygen source calcium peroxide is used.

Example 1: Use of an Oxygen-Providing Material with the Function of Skin Whitening on Sanitary Napkin Sanitary napkin comprises of an inner core and an outer coating layer. Inner core is used to fix functional ingredients, and functional ingredients can be evenly distributed on the inner surface of the inner core, at outer surface of the inner core 1 or within the inner cores.

The outer coating layer comprises of an inner layer and an outer layer. The inner layer is breathable structure made of skin-friendly materials, and the outer layer can be made of breathable materials and non-breathable materials. To achieve better effects of gradually releasing ROS and oxygen, the outer layer is preferably non-breathable material. Other preparation techniques adopt prior art.

Wherein the powders of whitening formulae 1-4 and comparison group 1-2 are used for the functional ingredients, so as to prepare different types of sanitary napkins;

The adding amounts of the functional ingredients are 1-1.2 g/tablet.

Experiment methods: 600 volunteers are recruited, and the sanitary napkins of the present invention and comparative examples are tested. The volunteers use these sanitary napkins 24 hours ceaselessly (short-time showering and the like are negligible). After 2 months, each fills out an assessment questionnaire independently. The ages of the volunteers range from 35 to 50, and the volunteers are divided into 6 groups.

Assessment of the Effects:

Not effective: the color of the skin of the private area shows no obvious change.

Effective: the extent of melanin sedimentation on the skin of the private area has decreased less than 50%, and the area of melanin sedimentation has decreased less than 30%; the skin is smooth and elastic, and the odor is alleviated.

Very effective: the color of the skin of the private area is obviously lightened, and the extent of melanin sedimentation has decreased more than 50%, and the area of melanin sedimentation has decreased more than 30%; the skin is smooth and elastic, and there is basically no odor.

TABLE 1

The application effects of the oxygen-providing materials with the function of skin whitening of the present invention on sanitary napkins

| | Whitening formula 1 | Whitening formula 2 | Whitening formula 3 | Whitening formula 4 | Comparison group 1 | Comparison group 2 |
|---|---|---|---|---|---|---|
| Not effective (person) | 5 | 1 | 6 | 0 | 50 | 45 |
| Effective (person) | 60 | 44 | 64 | 40 | 40 | 42 |
| Very effective (person) | 35 | 55 | 30 | 60 | 10 | 13 |
| Total effectiveness (%) | 95 | 99 | 94 | 100 | 50 | 55 |

Example 2: Use of an Oxygen-Providing Material with the Function of Skin Whitening on Chest Paste Chest paste comprises of an inner core and an outer coating layer. Inner core is used to fix functional ingredients, and functional ingredients can be evenly distributed on the inner surface of the inner core, at outer surface of the inner core 1 or within the inner cores.

The outer coating layer comprises of an inner layer and an outer layer. The inner layer is breathable structure made of skin-friendly materials, and the outer layer can be made of breathable materials and non-breathable materials. To achieve better effects of gradually releasing ROS and oxygen, the outer layer is preferably non-breathable material. Other preparation techniques adopt prior art.

Wherein the powders of whitening formulae 1-4 and comparison group 1-2 are used for the functional ingredients, so as to prepare different types of chest pastes;

The adding amounts of the functional ingredients are 0.3-0.5 g/tablet.

Experiment methods: 600 female volunteers are recruited, and the chest pastes of the present invention and comparative examples are tested. Each of the 600 females has experienced gestation, and has mammary areola, and blackened nipples.

The volunteers use these chest pastes 24 hours ceaselessly (short-time showering and the like are negligible). After 15 days, each fills out an assessment questionnaire independently. The ages of the volunteers range from 30 to 45, and the volunteers are divided into 6 groups.

Assessment of the Effects:

Not effective: the colors of the skins of the mammary areola, the nipples show no obvious change.

Effective: the diameter of the mammary areola has decreased less than 30%;

the color of the mammary areola has lightened less than 50%; the color of the top of the nipples has lightened less than 50%; and the color of the sides of the nipples has lightened less than 15%.

Very effective: the diameter of the mammary areola has decreased more than 30%; the color of the mammary areola has lightened more than 50%; the color of the top of the nipples has lightened more than 50%; and the color of the sides of the nipples has lightened more than 15%, and the colors of the mammary areola and the top of the nipples show flesh pink (those of females before pregnancy are this color).

Wherein the powders of whitening formulae 1-4 and comparison group 1-2 are used for the functional ingredients, so as to prepare different types of masks;

The adding amounts of the functional ingredients are 0.6-0.8 g/tablet.

Experiment methods: 150 female volunteers are recruited, and the volunteers are evenly divided into 6 groups. The masks of the present invention and comparative examples are tested. The ages of the volunteers range from 70 to 80. Each of these 150 females experience severe age pigments.

TABLE 2

The application effects of the oxygen-providing materials with the function of skin whitening of the present invention on chest pastes

|  | Whitening formula 1 | Whitening formula 2 | Whitening formula 3 | Whitening formula 4 | Comparison group 1 | Comparison group 2 |
|---|---|---|---|---|---|---|
| Not effective (person) | 6 | 2 | 5 | 1 | 46 | 40 |
| Effective (person) | 52 | 34 | 50 | 32 | 29 | 32 |
| Very effective (person) | 42 | 64 | 45 | 67 | 25 | 28 |
| Total effectiveness (%) | 94 | 98 | 95 | 99 | 54 | 60 |

Example 3: Use of an Oxygen-Providing Material with the Function of Skin Whitening on Mask Mask comprises of an inner core and an outer coating layer. Inner core is used to fix functional ingredients, and functional ingredients can be evenly distributed on the inner surface of the inner core, at outer surface of the inner core 1 or within the inner cores.

The outer coating layer comprises of an inner layer and an outer layer. The inner layer is breathable structure made of skin-friendly materials, and the outer layer can be made of breathable materials and non-breathable materials. To achieve better effects of gradually releasing ROS and oxygen, the outer layer is preferably non-breathable material. Other preparation techniques adopt prior art.

The volunteers use these masks 24 hours ceaselessly (short-time showering, eating and the like are negligible). After 15 days, each fills out an assessment questionnaire independently.

Assessment of the Effects:

Not effective: the areas and colors of the age pigments show no obvious changes

Effective: the colors of the age pigments have lightened less than 50%, and the areas has decreased less than 30%.

Very effective: the colors of the age pigments have lightened more than 50%, and the areas has decreased more than 30%.

TABLE 3

The application effects of the oxygen-providing materials with the function of skin whitening of the present invention

|  | Whitening formula 1 | Whitening formula 2 | Whitening formula 3 | Whitening formula 4 | Comparison group 1 | Comparison group 2 | Comparison group 3 | Comparison group 4 |
|---|---|---|---|---|---|---|---|---|
| Not effective (person) | 7 | 0 | 6 | 0 | 42 | 38 | 60 | 80 |
| Effective (person) | 46 | 30 | 46 | 28 | 26 | 29 | 22 | 18 |
| Very effective (person) | 50 | 70 | 48 | 72 | 31 | 33 | 18 | 2 |
| Total effectiveness (%) | 93 | 100 | 94 | 100 | 58 | 62 | 40 | 20 |

As can be seen from Table 3, addition of the activator TAED can yield more ROS $HO_2^-$ at room temperature, rendering better whitening effects.

TABLE 4

The application effects of the oxygen-providing materials with the function of skin whitening of the present invention on masks

| | Whitening formula 5 | Whitening formula 6 | Whitening formula 7 | Whitening formula 8 | Whitening formula 9 | Whitening formula 10 | Whitening formula 11 |
|---|---|---|---|---|---|---|---|
| Not effective (person) | 5 | 0 | 6 | 7 | 1 | 0 | 0 |
| Effective (person) | 33 | 30 | 35 | 30 | 29 | 40 | 36 |
| Very effective (person) | 65 | 70 | 62 | 66 | 70 | 60 | 64 |
| Total effectiveness (%) | 95 | 100 | 94 | 93 | 99 | 100 | 100 |

Example 4: Use of an Oxygen-Providing Material with the Function of Skin Whitening on Medical Dressing When the skin is wounded, the skin is wounded due to the external force at the wound, and the corium layer is damaged, and the ability of providing blood to the wound via blood is affected since the capillaries are damaged. At that time, the healing period of skin healing is prolonged due to lack of oxygen. In the meantime, in the wound healing process, spots may form along with the sedimentation of melanin, and even affection by anaerobe may be triggered.

Putting the oxygen-providing formula of the whitening formula 2 of the present invention into the interlayers of medical dressings (band-acids, wrapping sponge) provides oxygen at the wound to help the wound to heal, and can prevent the sedimentation of skin melanin to form spots, and inhibit the propagation and affection of anaerobe at the same time.

The above-mentioned oxygen-providing material is wrapped by a breathable container when being used; wherein the breathable container is a breathable net structure, providing active oxygen source to the wrapped skin at one hand, and being able to load the whitening product of the present invention into the interlayer and form a microspace between the breathable net structure and the skin, so that the powders do not directly contact the skin at the other hand. Said breathable container is any one of respirator, mask, facial mask, bra, chest paste, spill proof pad, sanitary napkin, diaper, panty liner, disposable hygiene product, band-aids, wrapping sponge, and box-shaped container. When the product of the present invention uses a box-shaped container as the carrier, powders can be put into the box, and the breathable materials (nonwovens, gauzes) are used to wrap the container. The intolayers of the above-mentioned wrapping container is used to load powders, rendering the powders separated from the skin and forming a microspace between the outer layer of the structure and the skin, so as to storage ROS and maintain a suitable concentration, continuously providing gaseous whitening ROS to the skin.

The above-mentioned oxygen-providing material with the function of skin whitening is a particle or powder or one-piece compressed from powders. The particle size of the product is 2000 meshes to 2 mm; the diameter of the above-mentioned oxygen-providing material with the function of skin whitening is larger than the pore size of the breathable container. Wherein the particle size of the oxygen-providing material with the function of skin whitening is preferably 40 to 80 meshes; wherein the particle size of the oxygen-providing material with the function of skin whitening is more preferably 60 meshes.

The usage amount of the oxygen-providing material with the function of skin whitening is 0.3 to 2 g/piece in usages except adult paper diaper; when used in adult paper diaper, the usage amount of the above-mentioned oxygen-providing material with the function of skin whitening is relatively large, i.e. 1 to 10 grams.

Compared to the prior art, the beneficial effects of the present invention are as follows.

(1) The oxygen-providing material with the function of skin whitening of the present invention, when used in sanitary napkin, can whiten the skin of female private area, rendering an obvious decline in the melanin sedimentation of the skin of the private area, and a decrease in the area of melanin sedimentation; the skin becomes smooth and elastic, and the odor is alleviated; and the total effectiveness is 94 to 100%;

(2) The oxygen-providing material with the function of skin whitening of the present invention, when used in chest pastes, have the effects of whitening the breast skin, and the colors of the mammary areolas and nipples are obviously lightened, and color of black brown turns into flesh pink; and the total effectiveness is 94 to 99%;

(3) The oxygen-providing material with the function of skin whitening of the present invention, when used in masks, renders the area of aging spot being obviously decreased, the color being obviously lightened, and the total effectiveness being 93 to 100%;

(4) The oxygen-providing material with the function of skin whitening of the present invention, when used in the interlayer of medical dressing (band-aids, wrapping sponage), provides oxygen at the wound to help the wound to heal, and at the same time prevents the melanin to precipitate at the skin to form pigmented spots, and inhibits the propagation and affection of anaerobes.

The above elaboration is embodiments of feasible examples of the present invention. However, those examples are not meant to limit the scopes of the present invention. Equivalents or alternations without departing from the spirit of the present invention should be contained in the scopes of the present invention.

The above-mentioned multiple effects relate to fully satisfying the statutory patentability elements of novelty and inventiveness. An application is filed according to the laws, and please grants the present invention patent application, to encourage invention.

What is claimed is:

1. A material providing skin-whitening gas, wherein said material comprises a solid oxygen source, a solid activator, and a solid catalyst; wherein:
- the solid oxygen source is selected from the group consisting of calcium peroxide, magnesium peroxide, sodium peroxide, potassium peroxide, sodium percarbonate, and calcium percarbonate;
- the solid activator is selected from the group consisting of tetraacetyl ethylene diamine (TAED), sodium nonanoyloxy benzene sulfonate (NOBS), tetraacetyl glycoluril, pentaacetyl glucose, N-acetyl phthalimid, 1-acetyl ethyl benzoate, triacetyl ethanolamine, and nonanoyl acetyl phenyl tosylate;
- the solid catalyst is catalase;
- a solid mass ratio between the activator and the solid oxygen source ranges from 0.5:100 to 10:100;
- a mass ratio between the solid catalyst and the solid oxygen source ranges from 0.5:100 to 5:100;
- and the material can react with fluid to produce whitening gas;
- wherein a citric acid can be further added into the material, and the mass ratio between the citric acid and the solid oxygen source ranges from (5-8):(2-5);
- wherein the material is placed in skin-contact products.

2. The material according to claim 1, wherein the solid mass ratio between the activator and the solid oxygen source ranges from 2:100 to 3:100; wherein the mass ratio between the solid catalyst and the solid oxygen source ranges from 1.5:100 to 2.5:100.

3. The material according to claim 1, wherein the material is in the form of particle, powder, or compressed powder, wherein the particle size of the material ranges from 2000 meshes to 2 mm.

4. The material according to claim 1, wherein the skin-contact products comprising respirator, mask, facial mask, bra, chest paste, spill proof pad, sanitary napkin, diaper, panty liner, disposable hygiene product, band-aids, wrapping sponge, and box-shaped container.

5. The material according to claim 1, wherein the whitening gas contains oxygen or reactive oxygen species (ROS).

6. A skin-whitening structure, wherein the skin-whitening structure is a breathable package wrapping the material according to claims 1, 2, 3, 4 or 5, wherein a particle size of the material ranges from 2000 meshes to 2 mm, the breathable package contains small pores, a diameter of the small pores are less than the particle size of the material, and the diameter of small pores are larger than the whitening gas.

* * * * *